United States Patent [19]

Farah

[11] 4,294,840
[45] Oct. 13, 1981

[54] KETAZOCINE ANESTHETIC METHOD OF USE

[75] Inventor: Alfred E. Farah, Shodack, N.Y.

[73] Assignee: Sterling Drug Inc., New York, N.Y.

[21] Appl. No.: 71,774

[22] Filed: Aug. 31, 1979

Related U.S. Application Data

[62] Division of Ser. No. 11,107, Feb. 12, 1979, Pat. No. 4,217,354.

[51] Int. Cl.$^3$ .................................. A61K 31/445
[52] U.S. Cl. .................................. 424/267; 546/97
[58] Field of Search ............... 424/267; 546/97

[56] References Cited

U.S. PATENT DOCUMENTS

| | | | |
|---|---|---|---|
| T941,017 | 12/1975 | Giering et al. | 424/267 |
| 3,936,462 | 2/1976 | Albertson | 546/97 |

OTHER PUBLICATIONS

*Chemical Abstracts*, 75:108,395v (1971) [Iwatsuki, K., et al., *Tohoku J. Exp. Med.* 1971, 104(2), 111–120].
*Chemical Abstracts*, 77:328c (1972) [Huidobro, F., *Arch. Int. Pharmacodyn. Ther.* 1971, 192(2), 362–364].
*Chemical Abstracts*, 85:186771k (1976) [Sternadel, Z., et al., *Ginekol. Pol.* 1976, 47(7), 769–773].
*Chemical Abstracts*, 86:83836b (1977) [Darbinyan, T., et al., *Eksp. Khir. Anesteziol.* 1976, (3), 73–78].
*Chemical Abstracts*, 87:127314g (1977) [Flerov, E., et al., *Anesteziol, Reanimatol.* 1977, (2), 12–25].
*Ama Drug Evaluations*, 3rd. Ed., Publishing Sciences Group, Inc., Littleton, Mass., 1977, pp. 263–284 and 285–324.
Physicians' Desk Reference, 34th Ed., Medical Economics Co., Oradell, NJ, 1980, pp. 1856–1858.
*Chemical Abstracts*, 58:861b (1963) [Jolly, C., *Brit. J. Anaesthesia*, 34, 571–575 (1962)].
*Chemical Abstracts*, 74:11609j (1971) [Hoffman, J. et al., *Arch. Int. Pharmacodyn Ther.* 1970, 186(2), 261–268].

*Primary Examiner*—Richard A. Schwartz
*Attorney, Agent, or Firm*—Theodore C. Miller; B. Woodrow Wyatt

[57] ABSTRACT

The method of producing anesthesia in a mammal comprising administering intravenously to the mammal an anesthetically effective amount of a pharmaceutically acceptable salt of racemic ketazocine or levo-ketazocine with or without diazepam premedication and the method of producing analgesia in a human which comprises administering intramuscularly to the human an anesthetically effective amount of at least 1 mg. of a pharmaceutically acceptable salt of racemic ketazocine or levo-ketazocine are disclosed.

3 Claims, No Drawings

KETAZOCINE ANESTHETIC METHOD OF USE

CROSS-REFERENCE TO RELATED APPLICATION

This application is a division of my co-pending application Ser. No. 11,107, filed Feb. 12, 1979 and now U.S. Pat. No. 4,217,354, issued Aug. 12, 1980.

BACKGROUND OF THE INVENTION

1. Field of the Invention

This invention relates to a method of producing anesthesia in a mammal using ketazocine.

2. Description of the Prior Art

U.S. Pat. No. 3,936,462, issued Feb. 3, 1976, describes racemic ketazocine (1,2,3,4,5,6-hexahydro-1-oxo-3-cyclopropylmethyl-9[sic, should read 8]-hydroxy-6(eq),11(ax)-dimethyl-2,6-methano-3-benzazocine) having the structural formula

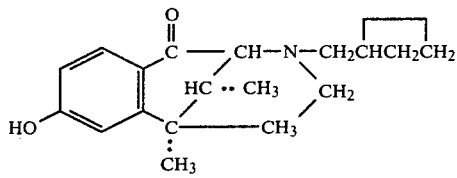

in Example 1 and dextro- and levo-ketazocine in Example 51 and salts thereof. Ketazocine and the other disclosed benzomorphans are described as "analgesic antagonists and analgesics". The patent does not describe or suggest the anesthetic use of ketazocine or any of the other disclosed benzomorphans, nor is any other prior description or suggestion of such use known to applicant.

General anesthetics depress the central nervous system and induce varying degrees of analgesia, depression of consciousness, skeletal muscle relaxation, and reduced reflex activity. The ideal general anesthetic should be stable, nonflammable, prompt acting, metabolically inert, and rapidly eliminated. It should provide adequate analgesia and muscular relaxation without producing excitement or any adverse effects on vital organs and systems, even during prolonged administration. Recovery of consciousness should occur quickly with no adverse after-effects or complications. No single agent presently available possesses all of these ideal characteristics [AMA Drug Evaluations, Third Edition, Publishing Sciences Group, Inc., Littleton, Mass., 1977, p. 285].

The general anesthetics are classified as inhalation anesthetics and intravenous anesthetics (ibid., chap. 18, pp. 285-299). Adjuncts to anesthesia, which are not themselves anesthetics, (ibid., chap. 19, pp. 300-324) including diazepam (ibid., p. 302) are frequently used with the general anesthetics. The commonly used intravenous anesthetics are the barbiturates, for example, thiopental sodium, and a nonbarbiturate, ketamine hydrochloride, which are seldom used alone but are generally used in combination with the inhalation anesthetics. Moreover, the barbiturates have little if any analgesic activity and ketamine hydrochloride has undesirable cerebrospinal fluid pressor, central nervous system excitatory, and hallucinatory and other psychic effects. There is therefore a need for an intravenous anesthetic which is self-sufficient as an anesthetic, which has good analgesic properties unlike the barbiturates and which does not have the undesirable effects of ketamine hydrochloride.

SUMMARY OF THE INVENTION

In a method aspect the invention is the method of producing anesthesia in a mammal which comprises administering intravenously to the mammal an anesthetically effective amount of a pharmaceutically acceptable salt of racemic ketazocine or levo-ketazocine.

In a further method aspect the invention is the method of producing anesthesia in a mammal which comprises administering diazepam intramuscularly to the mammal and subsequently administering intravenously to the mammal an anesthetically effective amount of a pharmaceutically acceptable salt of racemic ketazocine or levo-ketazocine.

In a further method aspect the invention is the method of producing anesthesia in a human which comprises administering to the human an anesthetically effective amount of at least 1 mg. of a pharmaceutically acceptable salt of racemic ketazocine or levo-ketazocine.

A related aspect of the invention is a composition for producing anesthesia in a mammal consisting essentially of an anesthetically effective concentration of a pharmaceutically acceptable salt of racemic ketazocine or levo-ketazocine in a pharmaceutically acceptable vehicle.

DETAILED DESCRIPTION OF THE INVENTION INCLUSIVE OF THE PREFERRED EMBODIMENTS

Racemic ketazocine has been tried as an analgesic in humans. Intramuscular administration of the drug at doses up to 0.6 mg. produced analgesia with rapid onset and short duration accompanied by sedation. In view of these results and in accordance with the present invention racemic ketazocine was tried as an intravenous anesthetic in preliminary tests in the dog and the monkey and found to be effective. Further testing in the dog showed that dextro-ketazocine had essentially no anesthetic effect. Accordingly, in further tests in the dog and the monkey only levo-ketazocine was tried and in trials in humans levo-ketazocine is contemplated to be used in preference to racemic ketazocine. The results of the following tests of levo-ketazocine in the dog and the monkey show that levo-ketazocine has a wide margin of effectiveness and safety as an anesthetic.

Tests in the Dog

Procedure: Eighteen untrained, randomly selected dogs (9 males and 9 females) weighing 8.2 kg to 16.4 kg were used. The following parameters were measured: systolic and diastolic blood pressure, heart rate, respiratory rate, onset and duration of anesthesia, muscle tone (rigid, flaccid, tremors, opisthotonus) and inhibition of the following reflexes: pinna (ear pinch), eyelid (tactile response), gag reflex, and the response of the fore and hind limb digits to pinching. Onset of anesthesia was determined as that time after the dog lost its righting reflex and duration as the time from loss of righting reflex to when the dog started moving about and attempted to get up. Upright time was determined as that time when the dog was standing up, although ataxia might still have been present. The dog was considered normalized when no apparent side effects were observed. Observations were also carried out regarding ocular effects (e.g. miosis, mydriasis, pupillary reaction to light, relaxation of the nictitating membrane), urination and defecation.

Five control readings (e.g. blood pressure, heart rate and respiration) were taken before the levo-ketazocine was administered. After injection of the levo-ketazocine the latter parameters were measured every five minutes up to sixty minutes and thereafter every fifteen minutes until the termination of the experiment (usually two hours). Observations regarding the other parameters were taken immediately after the levo-ketazocine was administered and continuously throughout the experiment. The studies were carried out with the dogs recumbent on their right sides. Blood pressures were taken with a standard infant's blood pressure cuff affixed to the upper left forelimb.

Levo-ketazocine methane sulfonate salt was dissolved in nonpyrogenic distilled water and administered intravenously (as a bolus) into the cephalic vein at doses (in terms of the base) of 0.125 mg/kg, 0.25 mg/kg, 1.0 mg/kg, 2.0 mg/kg and 4.0 mg/kg as a volume of 0.1 ml/kg of body weight. The pH values ranged from 4.45 to 3.1 at the 0.125 mg/kg and 4.0 mg/kg doses, respectively.

The results obtained at each dose were compared by paired data analysis with their respective controls. Since the same dogs were not used in all of the tests, group data analysis was used when comparing the results obtained between tests. A few of the dogs were used in more than one test; however, in no instance were they used sooner than one week after their previous testing. Student's t test was utilized for determining statistically significant differences.

Results: Onset of loss of righting reflex appeared to be dose-related (Table I). An increase in dose resulted in a decrease in time of onset. Average onset times ranged from 96 seconds to 22 seconds after medication. The difference noted between the onset times at the 0.125 mg/kg and 2.0 mg/kg and 4.0 mg/kg doses were significant ($P=0.05$). Average duration of anesthesia ranged from 22 minutes to 65 minutes at the 0.25 mg/kg and 4.0 mg/kg doses of levo-ketazocine, respectively. Although there was no direct dose-response relationship, there appeared to be a trend of increase in duration of anesthesia with increase in dose.

Inhibition of the pinna reflex was observed in all dogs at the 0.125 mg/kg, 2.0 mg/kg and 4.0 mg/kg doses of levo-ketazocine and in most of the dogs at the other doses (Table I). Inhibition of the eyelid response was observed in only one dog at 4.0 mg/kg. Inhibition of the gag reflex was observed at the 0.25 mg/kg through 2.0 mg/kg doses only. Inhibition of the forelimb reflex was observed in all of the dogs receiving 0.125 mg/kg, 2.0 mg/kg and 4.0 mg/kg of levo-ketazocine and in most of the dogs at 0.25 mg/kg and 1.0 mg/kg. Inhibition of the hind limb reflex was noted in all of the dogs receiving 0.125 mg/kg and 4.0 mg/kg and in most of the dogs at the other doses.

Transient decreases in systolic blood pressure were observed in most of the dogs at all doses. However, the decreases did not differ significantly from their respective premedication controls. With the exception of the 2.0 mg/kg dose, the maximal average decreases in systolic blood pressure were observed from 6 to 25 minutes after medication (Table II). At 2.0 mg/kg the maximal average decrease in systolic blood pressure was observed at 105 minutes after medication.

Decreases in diastolic blood pressure were observed in all dogs at all doses. With the exception of the 1.0 mg/kg dose, maximal average decreases in diastolic blood pressure occurred from 21 to 40 minutes after medication (Table II). The maximal average decrease in diastolic blood pressure observed with the 1.0 mg/kg dose was observed at 75 minutes after medication. There appeared to be a trend of enhanced decreases in diastolic blood pressure with increase in dose.

Decreases in heart rate were observed in all dogs at all doses. Maximal average decreases in heart rate were observed at 6 to 10 minutes after medication at the 0.125 mg/kg and 0.25 mg/kg doses. Thereafter, an increase in dose resulted in an increase in the time at which maximal average decreases in heart rate were observed (Table III). Maximal average decreases in heart rate ranged from 17% to 31% of controls but there did not appear to be a direct dose-response relationship. Significant decreases in heart rate were observed at 6 to 10 minutes and 16 through 35 minutes after medication at the 0.125 mg/kg and 2.0 mg/kg doses, respectively. At the 4.0 mg/kg dose of levo-ketazocine, a prolonged decrease in heart rate was observed from 16 to 55 minutes after medication.

Decreases in respiration were observed in all dogs at all doses. Maximal average decreases in respiration ranged from 46% to 69% of controls and did not appear to be dose-related. Maximal average decreases in respiration were observed within 1 to 5 minutes after medication at the 0.125 mg/kg and 1.0 mg/kg doses, at 6 to 10 minutes at the 0.25 mg/kg dose and at 21 to 25 minutes and 26–30 minutes at the 2.0 mg/kg and 4.0 mg/kg doses, respectively (Table IV). The decreases in respiration at the 0.125 mg/kg through 1.0 mg/kg doses differed significantly from their respective controls.

Rigidity was observed in all dogs receiving 0.25 mg/kg and 1.0 mg/kg of levo-ketazocine and in most of the dogs at the 2.0 mg/kg and 4.0 mg/kg doses (Table I). With the exception of the 4.0 mg/kg dose there was a trend of decrease in onset time of rigidity with an increase in dose. The rigidity persisted for 3 to 16 minutes after medication. The average onset of rigidity at 4.0 mg/kg was relatively greater than that noted at the other doses due primarily to its delayed onset (15 min) in one dog. However, the effect, when observed lasted for approximately 24 seconds. Flaccid muscle tone was observed in all dogs at all doses and always subsequent to rigidity. Tremors were observed in all of the dogs receiving 0.125 mg/kg and 4.0 mg/kg of levo-ketazocine and in most of the dogs at the other three doses. Neither onset time nor frequency of tremors was dose-related. However, there appeared to be a trend of increase in duration of tremors with increase in dose. Tremors were usually observed concomitantly with rigidity and were more pronounced during the inhalation phase of respiration. Opisthotonus was observed in two dogs at both the 2.0 mg/kg and 4.0 mg/kg doses. The effect was observed 15 to 30 seconds after medication and lasted 15 to 90 seconds.

Miosis was observed in all of the dogs at all doses (Table V). Onset of miosis was observed from 1.5 to 6 minutes after medication and persisted for 37 to 108 minutes. Mydriasis was observed only at the 0.25 mg/kg and 2.0 mg/kg doses and was always noted subsequent to miosis. Inhibition of the pupillary response was observed in 25 of the 28 dogs tested. Onset of inhibition was observed immediately after to six minutes after medication and persisted for 12 to 103 minutes after onset. There appeared to be a trend of earlier onset time and longer duration of inhibition with increase in dose. Partial relaxation of the nictitating membrane was observed in all dogs at all doses. Complete relaxation was observed in nearly half of the dogs and there did not appear to be a dose-response relationship. Onset of relaxation varied from 18 seconds to 15 minutes after medication and lasted from 5 to 100 minutes after onset.

Urination was observed in 11 dogs; the effect was not dose-related and occurred from 30 seconds to 90 minutes after medication. Normal bowel movement was observed in 20 of the 28 dogs and the effect was not dose-related. However, there appeared to be a trend toward an increase in episodes of loose stools with an increase in dose (Table V).

Tests in the Dog with Diazepam Premedication

Procedure: Fifteen untrained, randomly selected dogs (9 females and 6 males) weighing 8.4 to 16.4 kg were used. With the exception of the diazepam premedication, the methodology was essentially similar to that described above. Two basic studies were carried out: (1) that in which levo-ketazocine or diazepam was administered alone and (2) that in which the dogs were premedicated with diazepam prior to medication with levo-ketazocine. In all cases the levo-ketazocine was administered intravenously (as a bolus) into the cephalic vein at a dose (in terms of base) of either 0.25 mg/kg or 1.0 mg/kg. Diazepam was always injected intramuscularly into the right gluteus muscle at a dose of 0.5 mg/kg thirty minutes before the levo-ketazocine.

In the studies in which the levo-ketazocine or diazepam was administered alone, premedication control readings (e.g. blood pressure, heart rate and respiration) were taken at 25, 20, 15, 10 and 5 minutes. In the studies in which the dogs were premedicated with diazepam the usual premedication control readings were taken before the diazepam and thereafter five pre-levo-ketazocine (post diazepam) readings were taken at time intervals similar to those used when the drugs were administered alone. Immediately after injection of the levo-ketazocine, readings were taken every minute for the first five minutes, then every five minutes for the first hour and thereafter every fifteen minutes for the duration of the test. The studies were carried out with the dogs recumbent on their right sides. Blood pressures were taken with a standard infant's blood pressure cuff affixed to the upper left forelimb.

Solutions of levo-ketazocine methane sulfonate salt in non-pyrogenic sterile distilled water were prepared. The diazepam (Valium ®) used was from a commercially available multiple dose vial (5 mgm/ml), Roche Laboratories, Division of Hoffman LaRoche, Inc., Nutley, N.J.). Both the levo-ketazocine and diazepam were administered in volumes of 0.1 ml/kg of body weight. The pH values of the levo-ketazocine solutions were 4.2 to 4.5 and 3.3 to 3.8 for the 0.25 mg/kg and 1.0 mg/kg doses, respectively. Paired data analysis was used for comparing the responses obtained in a single test with its respective controls. Since the same animals were not used in each test, group data analysis was used to compare the results of the four tests. Student's t test was used for determining statistically significant differences.

Results: Diazepam premedication significantly ($<0.02$) increased the duration of prostration at the 1.0 mg/kg dose of levo-ketazocine (Table VI). Rigidity was observed in all of the dogs medicated with levo-ketazocine alone. Rigidity was reduced and eliminated at the 0.25 mg/kg and 1.0 mg/kg doses of levo-ketazocine respectively in the diazepam premedicated dogs. Tremors were observed in most of the dogs medicated with levo-ketazocine alone. No tremors were noted at either dose of levo-ketazocine after premedication with diazepam. Diazepam premedication significantly increased the duration of flaccid muscle tone at the 1.0 mg/kg dose of levo-ketazocine. Premedication with diazepam enhanced the inhibition of the various reflexes in most of the dogs.

Transient decreases in systolic blood pressure were observed at both doses in most of the dogs receiving levo-ketazocine alone. However, the decreases observed did not differ significantly from the respective premedication controls. Prolonged decreases ($<0.05$) in systolic blood pressure were observed at both doses of levo-ketazocine in the diazepam premedicated dogs (Table VII). Decreases in diastolic blood pressure were observed in all of the dogs receiving levo-ketazocine alone. However, the decreases observed did not differ significantly from their respective premedication controls. Significant ($<0.05$) decreases in diastolic blood pressure were observed from 6–10 minutes through 15–55 minutes and from 11–15 minutes through 31–35 minutes after medication at the 0.25 mg/kg and 1.0 mg/kg dose of levo-ketazocine, respectively after premedication with diazepam. Diazepam alone induced significant decreases in systolic ($<0.05$) and diastolic ($<0.02$) blood pressure at 26–30 minutes through 41–45 minutes and at 16–20 through 56–60 minutes after medication, respectively.

Decreases in heart rate were observed in all dogs medicated with the levo-ketazocine alone. Maximal average decreases in heart rate were observed at 6–10 minutes and 16–20 minutes after medication at the 0.25 mg/kg and 1.0 mg/kg doses of levo-ketazocine alone, respectively (Table VIII). However, the decreases observed did not differ significantly from their respective premedication controls. Significant ($<0.05$) decreases in heart rate were noted at the 1.0 mg/kg dose of levo-ketazocine after diazepam premedication. No significant decreases in heart rate were observed when the diazepam was administered alone.

Significant decreases in respiratory rate were observed from 1–5 minutes through 16–20 minutes after medication at both doses in the dogs administered the levo-ketazocine alone (Table IX). A transient but significant decrease in respiration was observed at 90 minutes after medication at the 0.25 mg/kg dose of levo-ketazocine after diazepam premedication. Diazepam premedication significantly enhanced both the degree and duration of decrease in respiration at the 1.0 mg/kg dose of levo-ketazocine. The maximal average decrease in respiration was observed at 1–5 minutes after medication in the dogs receiving 1.0 mg/kg of levo-ketazocine alone. In the diazepam premedicated dogs the maximal effect was observed at 26–30 minutes after medication. Significant decreases in respiration were observed at 21–25 minutes, 51–55 minutes and at 120 minutes after medication in the dogs receiving diazepam alone.

Miosis was observed in all of the dogs at both doses of levo-ketazocine either alone or after diazepam premedication (Table X). Miosis was observed in 4 of 5 dogs medicated with diazepam alone. Mydriasis was observed in only one dog at the 0.25 mg/kg dose of levo-ketazocine when administered either alone or after diazepam premedication. Relaxation of the nictitating membrane was enhanced in the diazepam premedicated dogs.

Urination and defecation were observed in 10 and 16 dogs respectively and the episodes of both effects were greater at the 1.0 mg/kg dose of levo-ketazocine when administered either alone or after diazepam premedication (Table X). Episodes of loose and mucoid stools were exacerbated by diazepam at the 1.0 mg/kg dose of levo-ketazocine.

Tests in the Monkey

Procedure: Rhesus monkeys (5 females and 2 males) weighing 3.4 to 4.9 kg were placed in a Foringer primate restraining apparatus. Both arms and legs were restrained. The areas to which the electrodes were attached were shaved and wiped with acetone prior to affixing the electrodes. At the termination of the experiment the areas were wiped with acetone and cleansed with 1:1000 benzalkonium chloride. Gold disk electrodes, 1 cm diameters, were used to carry out general EKG, EMG and EEG studies. Electrodes were coated with MS II conductivity gel (Medical Systems Corporation, Great Neck, N.Y.) and attached with adhesive tape which in turn was enclosed in masking tape.

The following parameters were studied: heart rate, respiratory rate, ocular effects (ptosis, mydriasis, miosis and lacrimation), body jerks and digital movement. In addition, the following reflexes were observed: eyelid response to touch, pupillary response to light and the forced air response (monkeys react markedly when the investigator blows on the facial area: FAR). Onset of anesthesia was determined as that time at which the head drooped and there was no apparent response to external audio and/or tactile stimuli. Duration of anesthesia was determined as that time at which spontaneous body movement and eyelid blinking was observed.

A Grass Model 7B Polygraph and Grass Model 7DAE D.C. Driver Amplifiers were utilized for all tests. Heart rate studies were carried out utilizing a Grass Model 7P6B EKG-Pulse Pre-Amplifier. The Lead II configuration was used in the latter studies and heart rates were read from the EKG pulse wave tracings. EMG studies were carried out using a Grass Model 7P3B Wide Band A.C. Pre-Amplifier and Integrator and a Grass Model 7P1E Low-level D.C. Pre-Amplifier. The EMG low-frequency input time constant was 0.04 sec. The integrator produced a signal proportional to fullwave rectification of the low-frequency input. The integrator time constant was 0.2 sec. Single electrodes were affixed to the medial and lateral surfaces of the left biceps and left biceps femoris muscles, respectively. The data obtained on the left biceps was in turn integrated. Episodes of body jerks were read directly from the EMG tracings. EEG studies were carried out using single electrodes attached to the left and right parietal areas of the scalp; an electrode placed medially over the occipital bone served as a common indifferent lead. The EEG input was coupled to two Grass Model 7P1E Low Level D.C. Pre-Amplifiers using a low-frequency time constant of 0.1 sec. EEG low level D.C. Pre-Amplifier sensitivity was calibrated so that fast and slow display was 50 $\mu$V/cm at 5 mm/sec and 50 mm/sec respectively.

Two basic studies were carried out: (1) that in which the levo-ketazocine was administered alone and (2) that in which the animals were medicated with diazepam prior to medication with levo-ketazocine. In all cases levo-ketazocine was injected into the saphenous vein (as a bolus) at a dose of either 0.25 mg/kg or 1.0 mg/kg. Diazepam was always injected intramuscularly into the right gluteus muscle at a dose of 0.5 mg/kg thirty minutes before the levo-ketazocine injection. In the studies in which levo-ketazocine was administered alone, five control readings were taken (e.g. at 30, 25, 20, 15 and 5 minutes) before the administration of the levo-ketazocine. In the studies in which the monkeys are premedicated with diazepam, five control readings were taken (e.g. at 30, 25, 20, 15 and 10 minutes) before the diazepam and thereafter the usual five pre-levo-ketazocine control readings were taken at intervals similar to the "drug alone" protocol. Immediately after injection of the levo-ketazocine, readings were taken every minute for the first five minutes. Thereafter, readings were taken every five minutes for the duration of the test (usually two to three hours).

Five minutes after the injection of levo-ketazocine the restraining apparatus was put into an inclined position. The apparatus remained in this position until the appearance of emergence symptoms. Restraining ties were placed behind the head and mid-lumbar area to support the monkey while in the inclined position. Since the monkeys were restrained, it was more difficult to ascertain the physical movements (e.g., digital and gross body movements) that are more apparent under unrestrained conditions and gross body movements were usually observed as body jerks. After removal from the restraining apparatus, the monkey was returned to the primate colony, placed on the floor and observed for any residual side effects e.g., ataxia, tremors, anorexia or sedation. Levo-ketazocine methane sulfonate salt was prepared in non-pyrogenic sterile distilled water. The diazepam (Valium ®) used was a commercially available sample (5 mg/ml) (Roche Laboratories, Division of Hoffman LaRoche, Inc., Nutley, N.J.). Both levo-ketazocine and diazepam were administered in volumes of 0.1 mg/kg. The pH values of the levo-ketazocine solutions were 4.2 to 4.5 and 3.7 to 3.9 for the 0.25 mg/kg and 1.0 mg/kg doses, respectively. Paired data analysis and Student's t test were used for determining statistically significant differences.

Results: Onset of anesthesia occurred sooner ($P<0.02$) and duration of anesthesia was more prolonged ($P<0.01$) at the 1.0 mg/kg dose of levo-ketazocine than at the 0.25 mg/kg dose of levo-ketazocine (both without premedication) (Table XI). A significant decrease in the onset of anesthesia was noted at the 0.25 mg/kg dose of levo-ketazocine after diazepam premedication. The duration of anesthesia at the 1.0 mg/kg dose of levo-ketazocine was significantly ($P<0.01$) greater than that noted at the 0.25 mg/kg dose in the diazepam premedicated monkeys. Inhibition of the eyelid, forced air and pupillary reflexes were enhanced after diazepam premedication.

Significant decreases in heart rate were observed from 3 to 55 minutes and 1 through 75 minutes and 90 minutes at the 0.25 mg/kg and 1.0 mg/kg doses of levo-ketazocine alone, respectively, (Table XII). Maximal average decreases in heart rate were observed at 20 minutes after medication with both doses of levo-ketazocine alone. Diazepam premedication enhanced both the degree and duration of bradycardia and increased the time at which maximal average decreases were observed at both doses of levo-ketazocine. Maximal average decreases in heart rate were noted at 25 minutes and 50 minutes after medication at the 0.25 mg/kg and 1.0 mg/kg doses of levo-ketazocine, respectively, in the diazepam premedicated monkeys.

Significant decreases in respiratory rate were observed from 2 to 40 minutes and 3 to 75 minutes and maximal average decreases at 5 and 4 minutes after medication at the 0.25 mg/kg and 1.0 mg/kg doses of levo-ketazocine alone, respectively, (Table XIII). Diazepam premedication enhanced both the intensity and duration of decreases in respiratory rate at both doses of levo-ketazocine. The time at which maximal average decrease was observed was unchanged after diazepam premedication at the 0.25 mg/kg dose of levo-ketazocine, however at the 1.0 mg/kg dose of levo-ketazocine the maximal effect was observed at 5 minutes after medication.

Mydriasis, lacrimation and ptosis were noted in all of the monkeys at both doses of levo-ketazocine either alone or after diazepam premedication (Table XIV). Miosis was observed in most of the monkeys and the effect was always noted subsequent to mydriasis. The onset of ptosis was decreased and the duration prolonged at the 1.0 mg/kg dose of levo-ketazocine after diazepam premedication. The duration of lacrimation observed at the 1.0 mg/kg dose of levo-ketazocine was prolonged after diazepam premedication. Diazepam premedication enhanced the degree of inhibition of the eyelid, forced air and pupillary response at both doses of levo-ketazocine (Table XV).

Body jerks were observed in all of the monkeys at the 1.0 mg/kg dose of levo-ketazocine alone and in 6 of 7 monkeys at the 0.25 mg/kg dose (Table XVI). 52 and 53 body jerks were observed respectively. The jerks occurred from 21 to 57 seconds after medication. Diazepam premedication attenuated both the number of body jerks and the number of monkeys in which the effect was elicited. The number of monkeys in which digital movement was observed was also reduced in the diazepam premedicated monkeys.

TABLE I

Observations on the Effect of Intravenously Administered Levo-ketazocine on Onset and Duration of Anesthesia, Muscle Tone and Reflex Inhibition in the Dog.

| Dose mg/kg (as base) | Route | N | PROSTATION Ave.[2] Onset Time (Secs.) | Ave.[3] Duration Time (Mins.) | Upright[4] Time (Mins.) | Normalization[5] Time (Mins.) | MUSCLE TONE RIGID Ave. Onset Time (Secs.) | Ave. Duration Time (Mins.) | $N/N_1$ | FLACCID Ave. Onset Time (Mins.) | Ave. Duration Time (Mins.) | $N/N_1$ | TREMORS Ave. Onset Time (Mins.) | Ave. Duration Time (Mins.) |
|---|---|---|---|---|---|---|---|---|---|---|---|---|---|---|
| 0.125 | I.V. | 5 | 96.0[1] ±33.0 | 34.8 ±5.8 | 36.4 ±5.4 | 59.0 ±9.9 | — | — | 0/5 | 3.9 ±1.4 | 20.1 ±5.7 | 5/5 | 4.9 ±2/6 | 7.7 ±2.5 |
| 0.25 | I.V. | 5 | 46.8 ±14.4 | 22.3 ±3.5 | 23.3 ±3.5 | 51.0 ±6.6 | 54.0 ±10.2 | 3.0 ±0.4 | 5/5 | 4.2 ±0.3 | 18.7 ±3.9 | 5/5 | 1.7 ±0.4 | 3.4 ±0.8 |
| 1.0 | I.V. | 5 | 31.8 ±7.2 | 59.7 ±14.4 | 60.4 ±14.4 | 94.8 ±8.5 | 49.0 ±8.3 | 3.7 ±1.5 | 5/5 | 5.9 ±2.3 | 39.5 ±9.3 | 5/5 | 0.5 ±0.1 | 5.4 ±2.7 |
| 2.0 | I.V. | 7 | 24.2 ±4.2 | 40.8 ±5.6 | 41.4 ±4.2 | 66.3 ±8.6 | 26.6 ±4.5 | 16.4 ±5.5 | 5/7 | 8.6 ±4.0 | 38.3 ±6.6 | 7/7 | 4.3 ±1.6 | 17.0 ±6.1 |
| 4.0 | I.V. | 6 | 22.2 ±1.0 | 64.5 ±14.3 | 91.7 ±24.5 | 99.7 ±22.0 | 246 ±216 | 11.7 ±5.6 | 4/6 | 7.7 ±4.0 | 71.2 ±21.8 | 6/6 | 13.8 ±5.9 | 20.4 ±7.6 |

| Dose mg/kg (as base) | Route | N | $N/N_1$ | REFLEX (INHIBITION) Pinna | Eyelid | Gag | Limbs Fore | Hind |
|---|---|---|---|---|---|---|---|---|
| 0.125 | I.V. | 5 | 5/5 | 5/5 | 0/5 | 0/5 | 5/5 | 5/5 |
| 0.25 | I.V. | 5 | 3/5 | 3/5 | 0/5 | 3/5 | 3/5 | 3/5 |
| 1.0 | I.V. | 5 | 4/5 | 4/5 | 0/5 | 2/5 | 4/5 | 4/5 |
| 2.0 | I.V. | 7 | 6/7 | 7/7 | 0/5 | 2/5 | 7/7 | 6/7 |
| 4.0 | I.V. | 6 | 6/6 | 6/6 | 1/5 | 0/5 | 6/6 | 6/6 |

[1] $\bar{x} \pm 1$ S.E.M.
[2] Onset is determined as that time after the dog loses its righting reflex.
[3] Duration is determined as that time at which the dog starts to move about and attempts to get up.
[4] Animal standing up but ataxic.
[5] No apparent side effects. At the 4.0 mg/kg dose and to a lesser degree at the 2.0 mg/kg dose the dogs at times may revert to an occasional transient period of slight ataxia.

TABLE II

The Effect of Intravenously Administered Levo-ketazocine on Blood Pressure in the Dog

| Dose mg/kg (as base) | N | | Control | Systolic and Diastolic Blood Pressure (mmHg) Post Medication (Time in Minutes) | | | | | | | |
|---|---|---|---|---|---|---|---|---|---|---|---|
| | | | | 1-5 | 6-10 | 11-15 | 16-20 | 21-25 | 26-30 | 31-35 | 36-40 |
| 0.125 | 5 | S | 154.7(1) ±8.2 | 148.8 ±3.8 | 144.8# ±6.8 | 146.8 ±9.8 | 147.4 ±9.7 | 147.2 ±8.9 | 149.2 ±11.5 | 152.8 ±12.8 | 150.6 ±10.8 |
| | | D | 86.5 ±2.5 | 82.4 ±3.2 | 75.4 ±3.2 | 75.8 ±4.1 | 77.8 ±6.1 | 72.2# ±4.2 | 76.6 ±6.7 | 75.2 ±7.8 | 72.3 ±4.5 |
| 0.25 | 5 | S | 143.6 ±15.1 | 156.2 ±9.2 | 154.6 ±10.8 | 152.6 ±10.9 | 154.4 ±8.4 | 152.6 ±11.2 | 152.6 ±11.2 | 150.6 ±10.9 | 159.8 ±13.6 |
| | | D | 92.1 ±8.8 | 80.2 ±8.9 | 83.6 ±8.7 | 91.0 ±7.4 | 87.8 ±6.9 | 83.2 ±8.7 | 75.6# ±6.6 | 76.6 ±6.3 | 85.0 ±7.5 |
| 1.0 | 5 | S | 166.5 ±13.3 | 183.4 ±14.7 | 180.0 ±9.7 | 166.2# ±10.7 | 169.6 ±14.4 | 173.0 ±14.8 | 183.0 ±15.0 | 174.0 ±13.4 | 176.2 ±10.5 |

TABLE II-continued

The Effect of Intravenously Administered Levo-ketazocine on Blood Pressure in the Dog

| Dose mg/kg (as base) | N | | Control | \multicolumn{8}{c}{Systolic and Diastolic Blood Pressure (mmHg) Post Medication (Time in Minutes)} |
|---|---|---|---|---|---|---|---|---|---|---|---|
| | | D | 94.2 ±7.0 | 78.4 ±10.8 | 81.6 ±8.5 | 78.2 ±9.4 | 84.2 ±3.9 | 92.4 ±3.0 | 89.4 ±2.8 | 89.8 ±2.9 | 84.0 ±7.6 |
| | | S | 149.2 ±7.8 | 149.6 ±7.6 | 148.1 ±10.2 | 150.0 ±10.2 | 148.0 ±8.7 | 144.4 ±7.2 | 146.5 ±7.0 | 145.4 ±5.7 | 150.1 ±5.6 |
| 2.0 | 7 | D | 86.5 ±7.0 | 88.7 ±5.2 | 76.4 ±6.1 | 68.9 ±9.5 | 71.9 ±9.8 | 68.3 ±8.7 * | 65.3# ±12.3 ** | 76.3 ±9.8 | 71.4 ±6.9 |
| | | S | 142.0 ±4.9 | 136.4 ±11.5 | 133.5 ±9.2 | 129.8# ±7.9 | 132.3 ±8.7 | 134.3 ±8.3 | 130.7 ±10.5 | 130.3 ±11.9 | 135.0 ±8.6 |
| 4.0 | 6 | D | 91.2 ±5.9 | 83.0 ±15.7 | 77.2 ±12.0 | 72.2 ±14.2 | 68.7 ±12.0 | 68.2 ±12.5 * | 67.5 ±12.3 * | 68.0 ±10.8 ** | 67.0# ±11.9 ** |

| | | | | 41–45 | 46–50 | 51–55 | 56–60 | 75 | 90 | 105 | 120 |
|---|---|---|---|---|---|---|---|---|---|---|---|
| | | S | 154.7(1) ±8.2 | 155.4 ±10.2 | 157.0 ±9.3 | 159.0 ±9.3 | 161.6 ±9.3 | 157.8 ±9.2 | 155.0 ±9.0 | 157.0 ±9.2 | 156.6 ±8.6 |
| 0.125 | S | S | 86.5 ±2.5 | 72.3 ±4.3 | 79.0 ±4.7 | 84.0 ±5.1 | 85.6 ±5.8 | 78.6 ±2.1 | 79.6 ±3.8 | 79.8 ±1.0 | 82.4 ±8.7 |
| | | S | 143.6 ±15.1 | 155.4 ±13.8 | 156.8 ±13.4 | 146.8 ±13.3 | 148.2 ±17.3 | 147.6 ±14.1 | 153.0 ±12.6 | 151.2 ±11.0 | 148.4 ±13.5 |
| 0.25 | S | S | 92.1 ±8.8 | 86.8 ±11.3 | 85.6 ±11.9 | 84.2 ±11.1 | 83.8 ±12.1 | 85.4 ±11.7 | 91.0 ±8.5 | 90.6 ±9.4 | 90.6 ±9.3 |
| | | S | 166.5 ±13.3 | 177.6 ±5.6 | 178.4 ±13.6 | 174.2 ±13.6 | 180.4 ±12.3 | 171.0 ±14.2 | 179.0 ±11.1 | 176.4 ±12.3 | 180.4 ±11.7 |
| 1.0 | S | S | 94.2 ±7.0 | 91.0 ±4.1 | 90.4 ±5.5 | 82.4 ±4.6 | 80.8 ±4.4 | 75.0# ±6.4 | 83.2 ±6.2 | 75.2 ±5.8 | 90.2 ±4.2 |
| | | S | 149.2 ±7.8 | 149.0 ±6.8 | 147.6 ±9.2 | 149.4 ±8.7 | 151.4 ±10.1 | 143.3 ±4.2 | 148.0 ±10.0 | 143.0# ±11.0 | 144.3 ±10.2 |
| 2.0 | 7 | S | 86.5 ±7.0 | 76.5 ±5.7 | 77.0 ±8.4 | 77.8 ±7.9 | 74.6 ±8.3 | 76.1 ±5.6 | 77.9 ±7.2 | 73.4 ±6.6 | 76.4 ±9.7 |
| | | S | 142.0 ±4.9 | 131.2 ±8.8 | 132.5 ±7.9 | 140.8 ±6.4 | 145.7 ±11.0 | 141.0 ±9.7 | 141.3 ±10.4 | 141.0 ±7.5 | 144.4 ±9.8 |
| 4.0 | S | S | 91.2 ±5.9 | 67.8 ±8.7 *** | 76.2 ±6.8 *** | 79.7 ±6.4 * | 75.2 ±11.2 | 76.5 ±11.8 | 72.8 ±8.7 * | 76.2 ±6.0 ** | 75.2 ±9.9 |

(1) Mean ± 1 S.E.M.
Maximal decrease Significance
*P ≦ 0.05
**P ≦ 0.12
***P ≦ 0.01

TABLE III

Observations on the Effect of Intravenously Administered Levo-ketazocine on Heart Rate in the Dog

| Dose mg/kg (as base) | N | Control | \multicolumn{8}{c}{Heart Rate (beats/min) Post Medication (time in minutes)} |
|---|---|---|---|---|---|---|---|---|---|---|
| | | | 1–5 | 6–10 | 11–15 | 16–20 | 21–25 | 26–30 | 31–35 | 36–40 |
| 0.125 | 5 | 91.0[1] ±10.9 | 72.0 ±5.2 | 65.60 ±2.6 * | 70.6 ±6.5 | 66.6 ±5.2 | 84.0 ±11.5 | 93.6 ±19.0 | 112.2 ±15.4 | 96.0 ±12.7 |
| 0.25 | 5 | 00.9 ±12.7 | 73.6 ±9.1 | 60.68 ±13.3 | 75.4 ±12.5 | 80.8 ±11.9 | 70.6 ±11.5 | 103.8 ±14.4 | 100.4 ±15.2 | 100.6 ±13.4 |
| 1.0 | 5 | 90.3 ±11.6 | 92.4 ±7.7 | 85.6 ±11.0 | 75.4 ±7.0 | 74.68 ±7.4 | 79.0 ±11.0 | 81.6 ±15.6 | 92.2 ±15.5 | 107.0 ±16.4 |
| 2.0 | 7 | 99.0 ±8.9 | 90.5 ±12.4 | 94.5 ±13.1 | 71.0 ±14.9 | 75.1 ±5.1 * | 70.9 ±4.5 *** | 66.58 ±5.4 *** | 76.7 ±9.7 ** | 86.3 ±10.9 |
| 4.0 | 6 | 104.6 ±8.6 | 98.0 ±9.0 | 81.7 ±2.9 | 82.0 ±1.0 | 86.0 ±7.0 | 70.1 ±7.0 * | 76.2 ±6.0 ** | 71.00 ±4.5 *** | 77.1 ±7.7 * |
| | | | 41–45 | 46–50 | 51–55 | 56–60 | 75 | 90 | 105 | 120 |
| 0.125 | 5 | 92.0[1] ±10.9 | 97.6 ±11.7 | 105.2 ±14.2 | 107.4 ±12.1 | 109.2 ±13.1 | 106.4 ±13.0 | 96.0 ±10.1 | 89.4 ±14.4 | 87.4 ±14.6 |
| 0.25 | 5 | 80.9 ±12.7 | 103.2 ±11.0 | 105.2 ±17.7 | 106.0 ±16.0 | 104.7 ±17.1 | 99.0 ±15.6 | 94.0 ±13.1 | 91.4 ±11.1 | 94.0 ±14.1 |

TABLE III-continued

Observations on the Effect of Intravenously Administered Levo-ketazocine on Heart Rate in the Dog

| Dose mg/kg (as base) | N | Control | Heart Rate (beats/min) Post Medication (time in minutes) | | | | | | | |
|---|---|---|---|---|---|---|---|---|---|---|
| 1.0 | 5 | 90.3 ±11.0 | 110.6 ±25.1 | 120.0 ±26.0 | 107.2 ±21.2 | 114.0 ±24.5 | 120.4 ±21.9 | 119.6 ±16.2 | 120.4 ±14.2 | 112.6 ±10.1 |
| 2.0 | 7 | 99.0 ±0.9 | 99.0 ±11.7 | 95.6 ±21.0 | 102.6 ±14.9 | 85.1 ±26.0 | 90.2 ±14.3 | 90.0 ±12.1 | 91.7 ±11.5 | 87.7 ±11.0 |
| 4.0 | 6 | 104.6 ±8.6 | 72.5 ±6.1 ** | 75.0 ±1.2 * | 02.1 ±4.4 * | 04.5 ±9.5 | 90.0 ±11.0 | 91.0 ±11.4 | 101.2 ±6.6 | 106.7 ±16.2 |

[1]Mean ± 1 S.E.M.
Maximal decrease Significance
*P ≦ 0.05
*P ≦ 0.02
***P ≦ 0.01

TABLE IV

Observations on the Effect of Intravenously Administered Levo-ketazocine on Respiratory Rate in the Dog

| Dose mg/kg (as base) | N | Control | Respiratory Rate (breaths/min) Post Medication (time in minutes) | | | | | | | |
|---|---|---|---|---|---|---|---|---|---|---|
| | | | 1-5 | 6-10 | 11-15 | 16-20 | 21-25 | 26-30 | 31-35 | 36-40 |
| 0.125 | 5 | 37.5[(1)] ±6.6 | 16.25 ±2.1 ** | 17.2 ±3.9 *** | 18.8 ±6.9 * | 26.6 ±13.7 | 26.6 ±18.1 | 45.6 ±21.3 | 56.6 ±26.5 | 59.6 ±22.9 |
| 0.25 | 5 | 44.4 ±6.4 | 16.6 ±2.2 * | 14.05 ±2.0 ** | 15.6 ±1.6 ** | 16.0 ±2.1 ** | 25.6 ±4.7 | 49.4 ±76.1 | 64.8 ±27.5 | 27.6 ±26.6 |
| 1.0 | 5 | 52.3 ±10.4 | 21.00 ±3.1 * | 22.0 ±3.3 * | 22.0 ±6.4 * | 21.4 ±31.8 * | 49.8 ±15.7 | 29.2 ±33.8 | 40.8 ±15.7 | 53.0 ±23.8 |
| 2.0 | 4.4 7 | 18.9 ±13.5 | 18.6 ±2.5 | 17.0 ±2.3 | 16.3 ±2.0 | 14.40 ±2.1 | 18.3 ±1.7 | 25.0 ±3.9 | 23.9 ±4.5 | ±3.9 |
| 4.0 | 6 | 30.5 ±12.4 | 30.0 ±5.1 | 25.2 ±8.4 | 25.0 ±8.8 | 26.0 ±8.8 | 25.3 ±8.7 | 21.00 ±6.6 | 22.8 ±7.0 | 30.7 ±14.1 |

| Dose mg/kg | | | 41-45 | 46-50 | 51-55 | 56-60 | 75 | 90 | 105 | 130 |
|---|---|---|---|---|---|---|---|---|---|---|
| 0.125 | 5 | 37.5[(1)] ±6.6 | 64.2 ±16.5 | 60.8 ±25.6 | 64.0 ±19.3 | 64.0 ±28.3 | 56.8 ±6.4 | 37.6 ±6.4 | 36.4 ±16.6 | 32.4 ±6.5 |
| 0.25 | 5 | 44.6 ±±21.8 | 19.4 ±25.6 | 19.6 ±22.7 | 66.4 ±20.8 | 61.0 ±20.8 | 47.4 ±1.9 | 44.6 ±4.9 | 24.3 | 27.0 |
| 1.0 | 5 | 2.2 ±10.4 | 45.5 ±17.9 | 45.6 ±17.1 | 50.0 ±18.4 | 45.2 ±15.7 | 28.6 ±4.7 | 33.8 ±7.2 | 32.4 ±7.0 | 43.8 ±6.3 |
| 2.0 | 7 | 44.4 ±13.4 | 27.3 ±4.8 | 34.3 ±11.8 | 33.0 ±6.6 | 34.7 ±12.6 | 37.9 ±14.7 | 36.4 ±14.2 | 34.0 ±15.4 | 32.3 |
| 4.0 | 6 | 36.5 ±12.4 | 27.0 ±12.5 | 23.3 ±7.8 | 26.0 ±7.1 | 25.5 ±5.5 | 26.2 ±8.1 | 23.9 ±8.5 | 24.5 ±5.6 | 29.0 ±34.5 |

[(1)]Mean ± 1 S.E.M.
Maximal decrease Significance
*P ≧ 0.05
**P ≧ 0.02
***P ≧ 0.01

TABLE V

Observations on Intravenously Administered Levo-ketazocine Induced Efftects in the Dog

| Dose mg/kg (as base) | Route | N | Miosis N/N₁[(1)] | Hydriasis N/N₁[(1)] | PUPILLARY Reaction (Inhibition) N/N₁[(1)] | NICTITAIING MEMB. (Relaxation) Partial N/N₁[(1)] | Complete N/N₁[(1)] | Opisthotonus N/N₁[(1)] | Urination N/N₁[(1)] | DEFECATION Normal N/N₁[(1)] | Loose N/N₁[(1)] | Mucoid N/N₁[(1)] |
|---|---|---|---|---|---|---|---|---|---|---|---|---|
| 0.125 | I.V. | 5 | 5/5 | 0/5 | 4/5 | 5/5 | 2/5 | 0/5 | 1/5 | 3/5 | 0/5 | 0/5 |
| 0.25 | I.V. | 5 | 5/5 | 1/5 | 5/5 | 5/5 | 1/5 | 0/5 | 2/5 | 4/5 | 1/5 | 0/5 |
| 1.0 | I.V. | 5 | 5/5 | 0/5 | 5/5 | 5/5 | 4/5 | 0/5 | 4/5 | 5/5 | 2/5 | 2/5 |
| 2.0 | I.V. | 7 | 7/7 | 2/7 | 6/7 | 7/7 | 3/7 | 2/7 | 2/7 | 3/7 | 3/7 | 0/5 |
| 4.0 | I.V. | 6 | 6/6 | 0/6 | 5/6 | 6/6 | 3/6 | 2/6 | 2/6 | 5/6 | 4/6 | 0/5 |

[(1)]N/N₁:
N = Number of dogs in which the effect was observed;
N₁ = Number of dogs tested.

TABLE VI

Observations on the Effects of Intravenously Administered Levo-ketazocine Alone and in Combination with Intramuscularly Administered Diazepam on Onset and Duration of Prostration Muscle Tone and Reflex Inhibition in the Dog

| | | | | PROSTRATION | | | | | RIGID | | | MUSCLE TONE FLACCID | | | TREMORS | | | REFLEX (Inhibition) | | | | |
|---|---|---|---|---|---|---|---|---|---|---|---|---|---|---|---|---|---|---|---|---|---|---|
| | Dose mg/kg | | | Ave. Onset[2] Time | Ave. Duration[3] Time | UP-RIGHT[4] Time | NORMAL-IZATION[5] Time | | Ave. Onset Time | Ave. Duration Time | | Ave. Onset Time | Ave. Duration Time | | Ave. Onset Time | Ave. Duration Time | | | | | Limbs | |
| Drug | (as base) | Route | N | (Secs) | (Mins) | (Mins) | (Mins) | N/N₁ | (Secs) | (Mins) | N/N₁ | (Secs) | (Mins) | N/N₁ | (Secs) | (Mins) | N/N₁ | Pinna | Eye-lid | Gag | Fore | Mind |
| A | 0.25 | I.V. | 5 | 46.8 ±14.4 | 22.3 ±3.5 | 23.3 ±3.5 | 51.0 ±6.6 | 5/5 | 54.0 ±10.2 | 30 ±0.4 | 5/5 | 4.2 ±0.3 | 28.7 ±3.9 | 5/5 | 1.7 ±0.4 | 3.4 ±0.8 | 3/5 | 3/5 | 0/5 | 3/5 | 3/5 | 3/5 |
| A | 0.26 | I.V. | | | | | | | | | | | | | | | | | | | | |
| B | 0.5 | I.M.[1] | 5 | 102.8 ±46.2 | 36.3 ±7.0 | 46.0 ±4.4 | 72.0 ±3.0 | 2/5 | 160. (n-2) | 4.0 ±3.0 | | 6.8 ±2.8 | 19.5 ±7.2 | 4/5 | — | — | 0/5 | 5/5 | 0/5 | 2/5 | 5/5 | 5/5 |
| A | 1.0 | I.V. | 5 | 31.8 ±7.2 | 59.7 ±14.4 | 60.4 ±8.5 | 94.8 ±8.3 | 5/5 ±2.3 | 49.0 ±1.5 | 8.7 | | 5.9 ±9.3 | 39.5 | 5/5 ±1.0 | 0.5 ±2.7 | 5.4 | 4/5 | 4/5 | 0/5 | 2/5 | 4/5 | 4/5 |
| A | 1.0 | I.V. | 5 | 19.8 ±1.2 | 100.9 ±6.6 | 101.2 ±6.7 | 114.0 | 0/5 | — | — | 5/5 | 3.8 ±1.0 | 74.8 ±5.7 | 5/5 | — | — | 0/5 | 5/5 | 1/5 | 5/5 | 5/5 | 5/5 |
| B | 0.5 | I.M. | 5 | — | — | — | — | 0/5 | — | — | 0/5 | — | — | 0/5 | — | — | 0/5 | 0/5 | 0/5 | 0/5 | 0/5 | 0/5 |
| B | 0.5 | I.M. | | | | | | | | | | | | | | | | | | | | |

[1]See note (1) Table VII.
[2]Onset is determined as that time after the dog loses itsrighting reflex.
[3]Duration is determined as that time at which the dog startsto move about and attempts to get up.
[4]Dog standing-up but ataxic.
[5]No apparent side effects.
Drug A: levo-ketazocine
Drug B: diazepam

TABLE VII

A Comparison of the Effects of Intravenously Administered Levo-ketazocine Alone and After Intramuscular Diazepam Premedication on Blood Pressure in the Dog

| Drug | Dose mg/kg (as base) | Route | N | Control | 1-5 | 6-10 | 11-15 | 16-20 | 21-25 | 26-30 | 31-35 | 36-40 |
|---|---|---|---|---|---|---|---|---|---|---|---|---|
| Levo-ketazocine | 0.25 | I.V. | S S | 143.6(2) ±15.1 | 156.2 ±9.2 | 154.6 ±10.9 | 152.6 ±10.9 | 154.4 ±8.4 | 152.6 ±11.2 | 152.6 ±11.2 | 150.6 ±10.9 | 159.8 ±13.6 |
| | | | D | 92.1 ±0.9 | 88.2 ±8.8 | 83.6 ±8.7 | 91.0 ±7.4 | 87.8 ±6.9 | 83.2 ±8.7 | 75.6# ±6.6 | 76.6 ±6.3 | 85.0 ±7.5 |
| Levo-ketazocine 0.025 Diazepam 0.5 | | I.V. I.M.(1) | S S | 147.4 ±5.4 | 137.6 ±6.6 | 133.4 ±5.0 *** | 137.0 ±3.2 ** | 135.0 ±2.6 * | 132.6# ±3.2 *** | 136.8 ±2.0 * | 138.6 ±2.7 | ±3.4 |
| | | | D | 77.5 ±6.1 | 66.2 ±3.0 | 64.6 ±4.5 *** | 63.8# ±4.2 *** | 64.4 ±3.9 *** | 64.8 ±4.5 | 69.2 ±3.0 * | 67.2 ±3.4 * | 65.4 ±2.6 * |
| Levo-ketazocine | 1.0 | I.V. | S S | 166.5 ±13.3 | 163.4 ±14.7 | 180.0 ±9.7 | 166.2# ±10.7 | 169.6 ±14.3 | 173.0 ±14.8 | 183.0 ±15.0 | 174.0 ±13.4 | 176.2 ±10.5 |
| | | | D | 94.2 ±7.0 | 78.4 ±10.0 | 91.6 ±0.5 | 70.3 ±9.4 | 84.2 ±3.9 | 92.4 ±3.0 | 89.4 ±2.0 | 89.9 ±2.9 | 84.0 ±7.6 |
| Levo-ketazocine 1.0 Diazepam 0.5 | | I.V. I.M.(1) | S S | 135.0 ±5.2 | 130.2 ±5.1 | 125.2 ±4.2 ** | 123.6 ±4.4 ** | 124.0 ±4.9 *** | 122.4 ±5.4 *** | 120.0 ±4.7 ** | 119.4 ±3.6 *** | 125.4 ±4.7 * |
| | | | D | 64.3 ±3.7 | 53.0 ±5.0 | 49.4 ±5.6 | 44.8 ±4.0 * | 45.4 ±5.1 | 45.0 ±4.9 * | 43.8 ±4.2 * | 45.2 ±4.5 * | 48.2 ±5.1 |
| Diazepam | 0.5 | I.M. | S S | 163.2 ±0.0 | 161.4 ±0.1 | 153.6 ±9.6 | 140.6 ±8.9 | 142.6 ±10.0 | 138.0 ±8.5 | 137.4 ±8.4 * | 134.6 ±7.4 * | 133.08 ±4.6 ** |
| | | | D | 95.1 ±5.9 | 88.4 ±0.6 | 89.4 ±7.8 | 92.6 ±6.7 | 79.4 ±7.6 ** | 73.6 ±6.1 *** | 72.8 ±6.5 *** | 71.6 ±5.9 *** | 73.6 ±4.5 **** |

| Drug | Dose mg/kg (as base) | Route | N | 41-45 | 46-50 | 51-55 | 56-60 | 75 | 90 | 105 | 130 |
|---|---|---|---|---|---|---|---|---|---|---|---|
| Levo-ketazocine | 0.25 | I.V. | S S | 143.6(2) ±15.1 | 155.4 ±13.9 | 156.8 ±13.4 | 146.8 ±13.3 | 148.2 ±17.3 | 147.4 ±14.1 | 153.0 ±12.8 | 151.2 ±11.8 | 148.4 ±13.5 |
| | | | D | 92.1 ±8.8 | 86.8 ±11.3 | 85.6 ±11.9 | 84.2 ±11.1 | 83.8 ±12.1 | 85.4 ±1.2 | 91.0 ±18.5 | 90.6 ±9.4 | 90.6 ±9.3 |
| Levo-ketazocine 0.025 Diazepam 0.5 | | I.V. I.M.(1) | S S | 147.4 ±5.4 *** | 139.0 ±4.5 *** | 140.0 ±4.3 | 143.0 ±4.9 | 145.0 ±6.9 | 144.0 ±6.6 | 143.0 ±6.5 | 144.4 ±7.8 | 146.4 ±7.2 |
| | | | D | 77.5 ±6.1 ** | 67.0 ±4.5 *** | 66.0 ±4.4 * | 70.0 ±3.6 | 73.2 ±6.9 | 72.0 ±8.0 | 71.4 ±6.0 | 72.4 ±7.5 | 75.4 ±6.3 |
| Levo-ketazocine | 1.0 | I.V. | S S | 166.5 ±13.3 | 177.6 ±9.6 | 178.4 ±13.0 | 174.2 ±13.6 | 180.4 ±12.3 | 173.8 ±14.2 | 179.8 ±11.1 | 170.4 ±12.3 | 180.4 ±11.7 |
| | | | D | 94.2 ±7.0 | 91.0 ±4.1 | 90.4 ±5.5 | 82.4 ±4.6 | 80.6 ±4.4 | 75.08 ±6.4 | 83.2 ±8.2 | 75.2 ±5.5 | 80.2 ±4.2 |
| Levo-ketazocine 1.0 Diazepam | | I.V. I.M.(1) | S S | 135.0 ±5.2 | 124.4 ±5.5 ** | 125.4 ±5.3 * | 123.0 ±5.5 * | 125.2 ±4.1 * | 132.0 ±3.0 | 135.0 ±1.9 | 134.0 ±1.2 | 134.4 ±1.5 |
| | | | D | 64.3 ±3.7 | 50.4 ±5.9 | 50.8 ±6.0 | 51.2 ±5.7 | 52.6 ±5.3 | 65.0 ±3.5 | 66.2 ±4.1 | 63.2 ±3.1 | 64.6 ±3.4 |
| Diazepam | 0.5 | I.M. | S S | 163.2 ±0.0 | 136.6 ±7.2 * | 140.2 ±10.2 | 143.6 ±10.0 | 145.2 ±9.5 | 149.2 ±9.4 | 149.4 ±9.4 | 150.2 ±9.3 | 152.0 ±9.6 |
| | | | D | 95.1 ±5.9 | 74.6 ±5.2 **** | 76.2 ±6.3 ** | 79.0 ±5.5 *** | 80.2 ±7.2 *** | 87.4 ±4.1 | 86.2 ±5.8 | 84.0 ±6.3 | 84.8 ±7.1 |

(1) Diazepam was administered 30 minutes before levo-ketazocine
(2) Mean ± 1 S.E.M.
\# Maximal decrease Significance
*P ≦ 0.05
**P ≦ 0.02
***P ≦ 0.01
****P ≦ 0.001

TABLE VIII

A Comparison of the Effects of Intravenously Administered Levo-ketazocine Alone and After Intramuscular Diazepam Premedication on Heart Rate in the Dog

| Drug | Dose mg/kg (as base) | Route | N | Controls | Heart Rate (Beats/min) (Post Medication (Time in Minutes) | | | | | | | |
|---|---|---|---|---|---|---|---|---|---|---|---|---|
| | | | | | 1-5 | 6-10 | 11-15 | 16-20 | 21-25 | 26-30 | 31-35 | 36-40 |
| Levo-ketazocine | 0.28 | I.V. | S | 80.9[2] ±12.7 | 73.6 ±9.1 | 68.68 ±13.3 | 75.4 ±12.5 | 80.8 ±11.9 | 70.6 ±11.5 | 103 ±16.4 | 100.4 ±15.2 | 100.6 ±13.4 |
| Levo-ketazocine Diazepam | 0.25 0.5 | I.V. I.M.[1] | S | 88.4 ±15.0 −4.4 | 65.6 ±3.9 | 62.0 ±3.1 | 62.8 ±7.0 | 61.6 ±5.0 | 62.0 ±4.5 | 61.4# ±4.8 | 62.0 ±2.8 | 62.0 |
| Levo-ketazocine | 1.0 | I.V. | S | 90.3 ±11.0 | 92.4 ±7.7 | 85.6 ±11.0 | 75.4 ±7.0 | 74.6# ±7.4 | 79.8 ±11.8 | 83.6 ±15.6 | 92.2 ±15.5 | 107.6 ±18.4 |
| Levo-ketazocine Diazepam | 1.0 0.8 | I.V. I.M.[1] | S | 79.6 ±3.6 | 73.2 ±4.7 | 68.0 ±4.0 *** | 64.0 ±2.8 ** | 62.4 ±4.1 *** | 60.0 ±3.6 *** | 57.68# ±3.3 *** | 56.4 ±3.6 | 69.2 ±6.2 |
| Diazepam | 0.8 | I.M. | S | 96.3 ±13.8 | 100.0 ±13.0 | 95.6 ±17.7 | 90.0 ±16.9 | 87.6 ±15.1 | 91.6 ±10.4 | 102.8 ±21.7 | 94.4 ±20.2 | 96.4 ±19.5 |
| | | | | | 41-45 | 46-50 | 51-55 | 56-60 | 75 | 90 | 105 | 120 |
| Levo-ketazocine | 0.28 | I.V. | S | 80.9[2] ±12.7 | 103.2 ±13.9 | 105.2 ±17.7 | 106 ±18.3 | 104.2 ±17.1 | 99.0 ±15.6 | 96.0 ±13.1 | 91.4 ±13.1 | 90 ±14.1 |
| Levo-ketazocine Diazepam | 0.28 0.5 | I.V. I.M.[1] | S | 80.4 ±18.0 | 62.0 ±4.4 | 91.2 ±16.3 | 89.8 ±16.6 | 82.8 ±18.6 | 80.4 ±14.3 | 76.8 ±10.7 | 72.6 ±19.8 | 79.0 ±11.7 |
| Levo-ketazocine | 1.0 | I.V. | S | 90.3 ±11.0 | 119.6 ±25.1 | 120.8 ±26.8 | 107.2 ±23.2 | 114.8 ±24.5 | 120.6 ±21.9 | 119.6 ±16.2 | 128.4 ±14.2 | 113. ±10. |
| Levo-ketazocine Diazepam | 1.0 0.9 | I.V. I.M.[1] | S | 79.6 ±3.6 * | 62.0 ±5.9 | 63.2 ±7.3 *** | 50.0 ±4.6 ** | 60.4 ±6.0 | 75.2 ±6.0 | 80.4 ±9.5 | 75.6 ±2.6 | 74.6 ±7.0 |
| Diazepam Diazepam | 0.8 | I.M. | S | 96.3 ±13.0 | 89.2 ±18.7 | 90.4 ±21.6 | 88.8 ±22.3 | 84.8# ±21.7 | 96.8 ±17.4 | 94.0 ±16.0 | 93.2 ±22.5 | 89.8 ±19.1 |

[1] See note (1) Table VII
[2] See note (2) Table VII
Maximal decrease Significance
*P ≦ 0.05
**P ≦ 0.02
***P ≦ 0.01

TABLE IX

A Comparison of the Effects of Intravenously Administered Levo-ketazocine Alone and After Intramuscular Diazepam Premedication on Respiratory Rate in the Dog

| Drug | Dose mg/kg (as base) | Route | N | Controls | Respiratory (breaths/min) Post-Medication (Time in Minutes) | | | | | | | |
|---|---|---|---|---|---|---|---|---|---|---|---|---|
| | | | | | 1-5 | 6-10 | 11-15 | 16-20 | 21-25 | 26-30 | 31-35 | 36-40 |
| Levo-ketazocine | 0.25 | I.V. | S | 44.6[2] ±6.4 | 16.6 ±2.2 * | 14.0# ±2.0 ** | 15.6 ±1.6 ** | 18.0 ±2.1 ** | 25.6 ±4.7 | 49.4 ±26.1 | 64.8 ±27.5 | 72.6 ±28.6 |
| Levo-ketazocine Diazepam | 0.25 0.5 | I.V. I.M.[1] | S | 44.2 ±9.5 ±1.0 | 22.8 ±3.2 | 18.8 ±3.6 | 21.2 ±3.6 | 20.8 ±1.9 | 18.2 ±2.2 | 18.0 ±1.4 | 17.2 ±3.4 | 17.0# |
| Levo-ketazocine | 1.0 | I.V. | S | 52.3 ±10.4 | 21.8# ±2.1 * | 22.0 ±3.7 * | 22.8 ±6.4 * | 23.6 ±6.4 * | 49.8 ±31.8 | 39.2 ±19.9 | 40.8 ±15.7 | 53.0 ±23.8 |
| Levo-ketazocine Diazepam | 1.0 0.5 | I.V. I.M.[1] | S | 30.3 ±1.8 ±0.8 | 15.6 ±0.6 *** | 14.0 ±0.8 *** | 13.6 ±1.1 *** | 14.0 ±0.8 *** | 12.8 ±0.8 *** | 11.2# ±0.8 **** | 14.8 ±1.6 **** | 17.2 ** |
| Diazepam | 0.5 | I.M. | S | 40.4 ±0.1 | 44.2 ±12.5 | 39.0 ±8.0 | 34.4 ±7.1 | 34.6 ±7.1 | 23.4# ±4.1 | 29.6 ±5.7 | 32.8 ±3.2 | 27.8 ±3.4 |
| | | | | | 41-45 | 46-50 | 51-55 | 56-60 | 75 | 90 | 105 | 120 |
| Levo-ketazocine | 0.25 | I.V. | S | 44.6[2] ±6.4 | 59.4 ±24.2 | 59.6 ±21.8 | 66.4 ±25.6 | 61.0 ±22.7 | 47.4 ±20.8 | 44.0 ±20.5 | 24.2 ±1.9 | 27.8 ±4.9 |
| Levo-ketazcine Diazepam | 0.25 0.5 | I.V. I.M.[1] | S | 44.2 ±9.5 ±4.7 | 22.8 ±7.2 | 27.2 ±5.5 | 24.8 ±8.5 | 28.8 ±5.2 | 26.8 ±3.4 | 24.8 ±1.8 * | 23.6 ±3.0 | 26.0 |
| Levo-ketazocine | 1.0 | I.V. | S | 52.3 ±10.4 | 49.8 ±17.9 | 48.6 ±17.1 | 50.0 ±18.4 | 43.2 ±15.7 | 28.8 ±4.7 | 33.8 ±7.2 | 32.4 ±7.0 | 43.0 ±8.3 |
| Levo-ketazocine Diazepam | 1.0 0.5 | I.V. I.M.[1] | S | 30.3 ±1.8 ±1.9 | 17.6 ±2.0 * | 16.6 ±1.2 ** | 14.4 ±2.2 *** | 18.0 ±2.2 * | 18.8 ±3.7 * | 21.6 ±2.9 | 22.4 ±1.4 * | 20.0 **** |
| Diazepam | 0.5 | I.M. | S | 40.4 | 25.6 | 26.2 | 26.0 | 26.6 | 27.2 | 25.6 | 25.0 | 24.2 |

TABLE IX-continued

A Comparison of the Effects of Intravenously Administered Levo-ketazocine Alone and After Intramuscular Diazepam Premedication on Respiratory Rate in the Dog

| Drug | Dose mg/kg (as base) | Route | N | Controls | Respiratory (breaths/min) Post-Medication (Time in Minutes) | | | | | | |
|---|---|---|---|---|---|---|---|---|---|---|---|
| | | | | ±8.1 | ±2.9 | ±3.8 | ±2.8* | ±2.6 | ±2.9 | ±2.0 | ±4.0 | ±2.9* |

[1]See Note [1] Table VII
[2]See Note [2] Table VII
\# Maximal decrease Significance
*$P \leq 0.05$
**$P \leq 0.02$
***$P \leq 0.01$
****$P \leq 0.001$

TABLE X

Observations on the Effects of Intravenously Administered Levo-ketazocine Alone and in Combination with Intravenously Administered Diazepam on Ocular Effects, Urination and Defecation in the Dog

| Drug | Dose mg/kg (as base) | Route | N | Miosis $N/N_1$[2] | Mydriasis $N/N_1$ | Pupillary Reaction (Inhibition) $N/N_1$ | Nictitating Membrane (Relaxation) | | Urination $N/N_1$ | Defecation | | |
|---|---|---|---|---|---|---|---|---|---|---|---|---|
| | | | | | | | Partial $N/N_1$ | Complete $N/N_1$ | | Normal $N/N_1$ | Loose $N/N_1$ | Mucoid $N/N_1$ |
| Levo-ketazocine | 0.25 | I.V. | 5 | 5/5 | 1/5 | 5/5 | 5/5 | 1/5 | 2/5 | 4/5 | 1/5 | 0/5 |
| Levo-ketazocine | 0.25 | I.V. | 5 | 5/5 | 1/5 | 5/5 | 5/5 | 3/5 | 1/5 | 2/5 | 0/5 | 0/5 |
| Diazepam | 0.5 | I.M.[1] | | | | | | | | | | |
| Levo-ketazocine | 1.0 | I.V. | 5 | 5/5 | 0/5 | 5/5 | 5/5 | 4/5 | 4/5 | 5/5 | 2/5 | 2/5 |
| Levo-ketazocine | 1.0 | I.V. | 5 | 5/5 | 0/5 | 5/5 | 5/5 | 5/5 | 3/5 | 5/5 | 5/5 | 4/5 |
| Diazepam | 0.5 | I.M. | | | | | | | | | | |
| Diazepam | 0.5 | I.M. | 5 | 4/5 | 0/5 | 0/5 | 0/5 | 0/5 | 0/5 | 0/5 | 0/5 | 0/5 |

[1]See Note [1] Table VII.
[2]$N/N_1$: N = Number of animals in which the effect was ovserved; $N_1$ = Number of animals tested.

TABLE XI

Observations on the Effect of Levo-ketazocine and Levo-ketazocine plus Diazepam on Onset and Duration of Anesthesia in the Monkey (n = 7)

| Test | Drug | Dose (mg/kg) (as base) | Route | Onset[3] (Minutes) | Duration[4] (Minutes) | Test | Relative Activity[5] | |
|---|---|---|---|---|---|---|---|---|
| | | | | | | | Onset | Duration |
| I | Levo-ketazocine | 0.25 | I.V. | 7.8[2] ±2.3 | 38.6 ±4.0 | I vs II I vs III | Sig. P = 0.02 Sig. P < 0.02 | N.S. Sig. P < 0.01 |
| II | Diazepam | 0.25 0.5 | I.V. I.M. | 0.66 ±0.12 | 49.3 ±9.3 | | | |
| III | Levo-ketazocine | 1.0 | I.V. | 3.9 ±1.6 | 71.9 ±8.0 | III vs IV | N.S. | N.S. |
| IV | Levo-ketazocine + Diazepam | 1.0 0.5 | I.V. I.M. | 1.3 ±0.19 | 93.6 ±16.0 | II vs IV | N.S. | Sig. P < 0.01 |

[1]Diazepam administered I.M. 30 minutes before levo-ketazocine.
[2]Mean ± S.E.M.
[3]Onset was determined as that time at which the head droops and there was no apparent response to the external audio and/or tactile stimuli.
[4]Duration was determined as that time at which spontaneous body movement and eyelid blinking was observed.
[5]Paired data analysis.

TABLE XII

A Comparison of the Effects of Intravenously Administered Levo-ketazocine Alone and After Intramuscular Diazepam Premedication on Heart Rate in the Monkey (N = 7)

| Drug | Dose mg/kg (as base) | Route | Controls | RESPIRATORY RATE (breaths/min) Post Medication (Time in Minutes) | | | | | | |
|---|---|---|---|---|---|---|---|---|---|---|
| | | | | 1 | 2 | 3 | 4 | 5 | 10 | 15 |
| Levo- | 0.25 | I.V. | 31.6[2] | 24.0 | 20.0 | 17.6 | 16.4 | 15.7# | 10.9 | 19.6 |

TABLE XII-continued

A Comparison of the Effects of Intravenously Administered Levo-ketazocine Alone and After Intramuscular Diazepam Premedication on Heart Rate in the Monkey (N = 7)

| Drug | Dose mg/kg (as base) | Route | Controls | RESPIRATORY RATE (breaths/min) Post Medication (Time in Minutes) | | | | | | |
|---|---|---|---|---|---|---|---|---|---|---|
| ketazocine | | | ±2.2 | ±2.9 *** | ±1.0 *** | ±1.8 *** | ±2.2 *** | ±2.2 *** | ±1.6 *** | ±1.9 *** |
| Levo-ketazocine | 0.25 | I.V. | 32.1 ±1.5 | 17.6 ±2.6 | 15.0 ±3.0 | 14.9 ±1.5 | 12.9 ±1.2 | 12.7# ±1.4 | 16.3 ±1.7 | 17.4 ±1.1 |
| Diazepam | 0.5 | I.M. | | *** | *** | **** | **** | **** | **** | |
| Levo-ketazocine | 1.0 | I.V. | 33.7 ±1.0 | 29.7 ±3.7 | 22.2 ±4.7 | 10.7 ±4.9 * | 11.4# ±3.7 * | 10.1 ±3.0 *** | 19.6 ±1.7 | 19.6 ±2.1 *** |
| Levo-ketazocine | 1.0 | I.V. | 30.0 ±1.7 | 9.3 ±1.2 | 10.0 ±1.6 | 10.9 ±1.6 | 10.0 ±1.6 | 9.0# ±1.4 | 11.6 ±1.2 | 12.9 ±1.4 |
| Diazepam | 0.5 | I.M. | | **** | **** | **** | **** | **** | **** | **** |
| | | | | 20 | 25 | 30 | 35 | 40 | 45 | 50 |
| Levo-ketazocine | 0.25 | I.V. | 31.6[2] ±2.2 | 20.0 ±1.5 *** | 22.6 ±2.4 *** | 22.6 ±3.2 *** | 24.1 ±3.6 | 23.9 ±3.4 ** | 20.1 ±3.1 | 29.0 ±3.3 |
| Levo-ketazocine | 0.25 | I.V. | 32.1 ±1.5 | 17.0 ±1.3 | 17.4 ±1.6 | 18.1 ±1.5 | 22.1 ±2.4 | 22.3 ±2.4 | 24.1 ±2.5 | 24.7 ±2.4 |
| Diazepam | 0.5 | I.M. | | **** | **** | **** | *** | *** | *** | * |
| Levo-ketazocine | 1.0 | I.V. | 33.7 ±1.0 | 20.9 ±2.3 ** | 19.1 ±2.3 *** | 10.0 ±1.4 **** | 19.0 ±2.2 *** | 10.3 ±2.0 **** | 20.6 ±3.1 *** | 21.4 ±3.1 ** |
| Levo-ketazocine | 1.0 | I.V. | 30.0 ±1.7 | 13.3 ±1.3 | 14.3 ±1.4 | 13.9 ±1.2 | 13.9 ±1.3 | 14.7 ±1.3 | 16.1 ±1.4 | 17.0 ±1.3 |
| Diazepam | 0.5 | I.M. | | **** | **** | **** | **** | **** | **** | **** |
| | | | | 55 | 60 | 65 | 70 | 75 | 80 | 85 |
| Levo-ketazocine | 0.25 | I.V. | 31.6[2] ±2.2 | 32.0 ±2.7 | 34.6 ±2.9 | 31.7 ±3.9 | 31.5 ±3.0 | 32.3 ±3.3 | 20.0 ±4.1 | 29.2 ±3.7 |
| Levo-ketazocine | 0.25 | I.V. | 32.1 ±1.5 | 26.1 ±2.7 * | 26.9 ±2.7 | 26.9 ±3.1 | 26.6 ±3.2 | 28.1 ±3.1 | 28.1 ±3.1 | 29.7 ±3.5 |
| Diazepam | 0.5 | I.M. | | | | | | | | |
| Levo-ketazocine | 1.0 | I.V. | 33.7 ±1.0 | 22.1 ±2.9 *** | 24.3 ±3.0 ** | 26.0 ±3.3 * | 27.3 ±3.9 | 29.0 ±2.6 * | 35.7 ±2.3 | 34.3 ±3.0 |
| Levo-ketazocine | 1.0 | I.V. | 30.0 ±1.7 | 17.7 ±1.2 | 10.7 ±1.5 | 19.0 ±1.3 | 20.0 ±1.1 | 20.3 ±1.3 | 21.0 ±1.5 | 21.3 ±1.5 |
| Diazepam | 0.5 | I.M. | | **** | **** | **** | **** | **** | **** | **** |
| | | | | 90 | 95 | 100 | 105 | 110 | 115 | 120 |
| Levo-ketazocine | 0.25 | I.V. | 31.6[2] ±2.2 | 29.2 ±3.2 | 29.0 ±3.6 | 30.6 ±3.3 | 20.0 ±2.5 | 20.0 ±2.5 | 20.6 ±2.4 | 29.2 ±2.9 |
| Levo-ketazocine | 0.25 | I.V. | 32.1 ±1.5 | 29.1 ±3.6 | 20.6 ±3.5 | 30.7 ±3.5 | 31.6 ±3.3 | 30.1 ±3.2 | 30.3 ±3.0 | 30.4 ±2.3 |
| Diazepam | 0.5 | I.M. | | | | | | | | |
| Levo-ketazocine | 1.0 | I.V. | 33.7 ±1.0 | 35.3 ±2.4 | 33.0 ±2.6 | 33.0 ±4.2 | 31.2 ±2.0 | 24.3 ±4.0 | 20.7 ±2.0 | 27.8 ±1.7 |
| Levo-ketazocine | 1.0 | I.V. | 30.0 ±1.7 | 24.0 ±2.2 | 24.4 ±2.6 | 26.4 ±2.87 | 25.7 ±2.0 | 26.9 ±2.0 | 25.3 ±2.5 | 25.9 ±3.0 |
| Diazepam | 0.5 | I.M. | | *** | ** | | * | | * | |

[1]Diazepam administered I.M. 30 minutes before levo-ketazocine
[2]Mean ± 1 S.E.M.
Maximal decrease
Significance
*$P \leq 0.05$
**$P \leq 0.02$
***$P \leq 0.01$
****$P \leq 0.001$

TABLE XIII

A Comparison of the Effects of Intravenously Administered Levo-ketazocine Alone and After Intramuscular Diazepam Premedication on Respiration in the Monkey (N = 7)

| Drug | Dose mg/kg (as base) | Route | Controls | Heart Rate (beats/min) Post Medication (Time in Minutes) | | | | | | |
|---|---|---|---|---|---|---|---|---|---|---|
| | | | | 1 | 2 | 3 | 4 | 5 | 10 | 15 |
| A | 0.25 | I.V. | 214.3[2] ±12.6 | 194.3 ±9.5 | 197.1 ±13.4 | 160.0 ±13.8 ** | 162.9 ±11.1 * | 160.6 ±9.6 * | 145.7 ±9.5 *** | 142.9 ±11.1 *** |

TABLE XIII-continued

A Comparison of the Effects of Intravenously Administered Levo-ketazocine Alone and After Intramuscular Diazepam Premedication on Respiration in the Monkey (N = 7)

| Drug | Dose mg/kg (as base) | Route | Controls | Heart Rate (beats/min) Post Medication (Time in Minutes) | | | | | | |
|---|---|---|---|---|---|---|---|---|---|---|
| A | 0.25 | I.V. | 216.0 ±10.5 | 197.1 ±10.2 | 108.6 ±9.6 | 162.9 ±12.7 | 162.9 ±10.2 | 171.4 ±8.6 | 142.9 ±8.1 | 137.1 ±6.0 |
| B | 0.5 | I.M. | | | | * | *** | *** | *** | ****. |
| A | 1.0 | I.V. | 215.3 ±7.2 | 100.0 ±10.0 *** | 160.0 ±20.0 * | 154.3 ±17.0 ** | 154.3 ±12.1 *** | 162.9 ±11.1 ** | 145.7 ±12.1 ** | 137.1 ±11.1 *** |
| A | 1.0 | I.V. | 211.4 ±12.9 | 170.0 ±11.3 **** | 145.7 ±14.3 ** | 160.6 ±5.9 *** | 191.4 ±9.6 *** | 157.1 ±11.9 *** | 124.3 ±6.1 **** | 124.3 ±8.7 **** |
| B | 0.5 | I.M. | | | | | | | | |
|  |  |  |  | 20 | 25 | 30 | 35 | 40 | 45 | 50 |
| A | 0.25 | I.V. | 214.3[2] ±12.6 | 134.3# ±10.4 *** | 140.0 ±14.5 *** | 142.9 ±11.9 *** | 137.1 ±9.2 **** | 154.3 ±16.2 *** | 154.3 ±16.2 *** | 160.0 ±14.5 *** |
| A | 0.25 | I.V. | 216.0 ±10.5 | 125.7 ±9.5 **** | 122.9# ±8.1 **** | 122.9 ±9.2 **** | 122.9 ±9.2 **** | 125.7 ±11.3 **** | 131.4 ±13.7 **** | 137.1 ±13.4 *** |
| B | 0.5 | I.M. | | | | | | | | |
| A | 1.0 | I.V. | 215.3 ±7.2 | 128.6# ±8.6 **** | 137.1 ±11.1 *** | 128.7 ±8.6 **** | 137.1 ±11.1 *** | 137.3 ±11.1 *** | 145.7 ±12.1 *** | 145.7 ±12.1 *** |
| A | 1.0 | I.V. | 211.4 ±12.9 | 121.4 ±7.0 **** | 110.6 ±7.7 **** | 111.4 ±4.0 **** | 117.1 ±6.8 *** | 111.4 ±7.4 **** | 111.4 ±7.4 **** | 109.6# ±5.9 **** |
| B | 0.5 | I.M. | | | | | | | | |
|  |  |  |  | 55 | 60 | 65 | 70 | 75 | 80 | 85 |
| A | 0.25 | I.V. | 214.3[2] ±12.6 | 108.6 ±13.0 * | 200.0 ±19.5 | 190.0 ±12.4 | 206.7 ±12.3 | 203.3 ±15.0 | 200.0 ±16.7 | 208 ±16.2 |
| A | 0.25 | I.V. | 216.0 ±10.5 | 151.4 ±16.2 *** | 148.6 ±13.7 *** | 160.0 ±13.0 * | 168.6 ±15.0 * | 174.3 ±14.9 | 180.0 ±14.5 | 105.7 ±15.6 |
| B | 0.5 | I.M. | | | | | | | | |
| A | 1.0 | I.V. | 215.3 ±7.2 | 154.3 ±12.1 *** | 145.7 ±12.1 *** | 160.0 ±20.0 * | 160.0 ±20.0 * | 180.0 ±13.1 ** | 170.0 ±18.4 | 170.0 ±18.4 |
| A | 1.0 | I.V. | 211.4 ±12.9 | 108.6 ±9.9 **** | 100.6 ±8.6 **** | 111.4 ±0.6 **** | 117.1 ±0.1 **** | 121.4 ±10.3 **** | 124.3 ±10.7 **** | 130.0 ±10.9 **** |
| B | 0.5 | I.M. | | | | | | | | |
|  |  |  |  | 90 | 95 | 100 | 105 | 110 | 115 | 120 |
| A | 0.25 | I.V. | 214.3[2] ±12.6 | 204.0 ±17.2 | 192.0 ±22.4 | 200.0 ±19.0 | 200.0 ±17.4 | 200.0 ±22.8 | 200.0 ±11.0 | 224 ±14.7 |
| A | 0.25 | I.V. | 216.0 ±10.5 | 191.4 ±9.6 | 200.0 ±10.7 | 220.0 ±10.7 | 222.9 ±11.9 | 214.3 ±12.9 | 222.9 ±11.9 | 225.7 ±13.6 |
| B | 0.5 | I.M. | | | | | | | | |
| A | 1.0 | I.V. | 215.3 ±7.2 | 180.0 ±13.1 ** | 200.0 ±20.0 | 192.0 ±22.4 | 100.0 ±24.5 | 160.0 ±20.0 | 160.0 ±20.0 | 100.0 ±10.0 |
| A | 1.0 | I.V. | 211.4 ±12.9 | 130.6 ±12.0 *** | 144.3 ±14.0 *** | 154.3 ±18.4 * | 154.3 ±18.4 * | 154.3 ±17.0 * | 148.6 ±15.6 ** | 151.4 ±14.4 ** |
| B | 0.5 | I.M. | | | | | | | | |

[1]See note (1) Table XII
[2]See note (2) Table XII
Maximal decrease
Significance
*P ≤ 0.05
**P ≤ 0.02
***P ≤ 0.01
****P ≤ 0.001
Drug A: levo-ketazocine
Drug B: diazepam

TABLE XIV

Observations on the Effects of Intravenously Administered Levo-ketazocine Alone and in Combination with Intramuscularly Administered Diazepam on Frequency, Onset and Duration of Ocular Effects in the Monkey (N = 7)

| Drug | Dose (mg/kg) (as base) | Route | HYDRIASIS | | | MIOSIS | |
|---|---|---|---|---|---|---|---|
|  |  |  | ONSET (secs.) | DURATION (mins.) | FREQUENCY n/n$_1$ | DURATION (mins.) | FREQUENCY n/n$_1$ |
| Levo-ketazocine | 0.25 | I.V. | 45.0[2] ±7.2 | 67.1 ±10.5 | 7/7 | 25.7 ±13.0 | 5/7 |
| Levo-ketazocine | 0.25 | I.V. } | 43.6 | 82.6 | 7/7 | 21.4 | 4/7 |

TABLE XIV-continued

Observations on the Effects of Intravenously Administered Levo-ketazocine Alone and in Combination with Intramuscularly Administered Diazepam on Frequency, Onset and Duration of Ocular Effects in the Monkey (N = 7)

| Drug | Dose (mg/kg) (as base) | Route | | | | | |
|---|---|---|---|---|---|---|---|
| Diazepam | 0.5 | I.M. | ±7.9 | ±14.0 | | ±9.4 | |
| Levo-ketazocine | 1.0 | I.V. | <60 (N = 7) | 48.6 ±8.7 | 7/7 | 30.7 ±12.1 | 6/7 |
| Levo-ketazocine | 1.0 | I.V. ⎫ | 54.3 ±5.7 | 55.7 ±15.8 | 7/7 | 66.4 ±19.2 | 6/7 |
| Diazepam | 0.5 | I.M. ⎭ | | | | | |

| | Dose (mg/kg) | | LACRIMATION | | | PTOSIS | | |
|---|---|---|---|---|---|---|---|---|
| Drug | (as base) | Route | ONSET (mins.) | DURATION (mins.) | FREQUENCY n/n₁ | ONSET (mins.) | DURATION (mins.) | FREQUENCY n/n₁ |
| Levo-ketazocine | 0.25 | I.V. | 3.3 ±1.2 | 72.6 ±7.4 | 7/7 | 3.9 ±1.9 | 52.0 ±9.7 | 7/7 |
| Levo-ketazocine | 0.25 | I.V. ⎫ | 8.0 ±3.1 | 71.1 ±12.0 | 7/7 | 0.93 ±0.07 | 83.4 ±11.2 | 7/7 |
| Diazepam | 0.5 | I.M. ⎭ | | | | | | |
| Levo-ketazocine | 1.0 | I.V. | 2.9 ±0.55 | 117.5 ±10.2 | 7/7 | 4.3 ±1.6 | 86.4 ±11.8 | 7/7 |
| Levo-ketazocine | 1.0 | I.V. ⎫ | 3.6 ±1.7 | 138.6 ±14.4 | 7/7 | <1.0 (N = 7) | 141.9 ±16.1 | 7/7 |
| Diazepam | 0.5 | I.M. ⎭ | | | | | | |

[1] Diazepam administered I.M. 30 minutes before levo-ketazocine.
[2] Mean ± 1 S.E.M.
[3] n/n₁: n = No. of monkeys in which effect was observed; n₁ = No. of monkeys tested.

TABLE XV

Effect of Diazepam Premedication on Levo-ketazocine Induced Inhibition of Eyelid, Forced Air and Pupillary Reflexes in the Monkey (N = 7)

| Drug | Dose (mg/kg) (as base) | Route | EYELID N/N₁[2] | | | FORCED AIR N/N₁ | | | PUPIL N/N₁ | | |
|---|---|---|---|---|---|---|---|---|---|---|---|
| | | | Partial | Complete | Total (P + C) | Partial | Complete | Total (P + C) | Partial | Complete | Total (P + C) |
| Levo-ketazocine | 0.25 | I.V. | 3/7 | 4/7 | 7/7 | 4/7 | 3/7 | 7/7 | 3/7 | 2/7 | 5/7 |
| Levo-ketazocine | 0.25 | I.V. ⎫ | 1/7 | 6/7 | 7/7 | 2/7 | 5/7 | 7/7 | 3/7 | 3/7 | 6/7 |
| Diazepam | 0.5 | I.M. ⎭ | | | | | | | | | |
| Levo-ketazocine | 1.0 | I.V. | 5/7 | 2/7 | 7/7 | 3/7 | 4/7 | 7/7 | 1/7 | 1/7 | 2/7 |
| Levo-ketazocine | 1.0 | I.V. ⎫ | 0/7 | 7/7 | 7/7 | 0/7 | 7/7 | 7/7 | 3/7 | 4/7 | 7/7 |
| Diazepam | 0.5 | I.M. ⎭ | | | | | | | | | |

[1] Diazepam administered I.M. 30 minutes before levo-ketazocine
[2] N/N₁: N = No. of monkeys in which effect was observed; N₁ = No. of monkeys tested.

TABLE XVI

Observations on the Effect of Diazepam Premedication on Levo-ketazocine Induced Digi-Movement and Body Jerks in the Monkey (N = 7)

| Drug | Dose (mg/kg) (as base) | Route | Onset time (secs.) | Body Jerks TIME INTERVALS (MINUTES) | | | | | | | | | | N/N₁[2] | Digital movement N/N₁[2] |
|---|---|---|---|---|---|---|---|---|---|---|---|---|---|---|---|
| | | | | 0-1 | 1-2 | 2-3 | 3-4 | 4-5 | 5-6 | 6-7 | 7-8 | 8-9 | 9-10 | | |
| Levo-ketazocine | 0.25 | I.V. | 39.3[3] ±7.4 | 10 | 15 | 15 | 5 | 1 | 1 | — | — | 1 | 1 | 6/7 | 6/7 |
| Levo-ketazocine | 0.25 | I.V. ⎫ | 36.4 ±24.9 | 4 | — | — | 4 | — | — | — | — | — | — | 3/7 | 1/7 |
| Diazipam | 0.5 | I.M. ⎭ | | | | | | | | | | | | | |
| Levo-ketazocine | 1.0 | I.V. | 56.6 ±17.9 | 7 | 21 | 9 | 6 | 4 | 1 | — | — | — | 3 | 7/7 | 2/7 |
| Levo-ketazocine | 1.0 | I.V. ⎫ | 21.3 ±8.1 | 6 | — | — | 1 | — | — | — | — | — | — | 5/7 | 1/7 |
| Diazipam | 0.5 | I.H. ⎭ | | | | | | | | | | | | | |

| | | | | 10-11 | 11-12 | 12-13 | 13-14 | 14-15 | Total (15 min) | | |
|---|---|---|---|---|---|---|---|---|---|---|---|
| Levo-ketazocine | 0.25 | I.V. | 39.3[3] ±7.4 | 1 | — | 1 | 1 | — | 52 | 6/7 | 6/7 |
| Levo-ketazocine | 0.25 | I.V. ⎫ | 36.4 ±24.9 | — | — | — | — | — | 8 | 3/7 | 1/7 |
| Diazepam | 0.5 | I.M. ⎭ | | | | | | | | | |
| Levo-ketazocine | 1.0 | I.V. | 56.6 ±17.9 | 2 | — | — | — | — | 53 | 7/7 | 2/7 |

TABLE XVI-continued

Observations on the Effect of Diazepam Premedication on Levo-ketazocine Induced Digi-Movement and Body Jerks in the Monkey (N = 7)

| Drug | Dose (mg/kg) (as base) | Route | Onset time (secs.) | Body Jerks TIME INTERVALS (MINUTES) | | | | | | $N/N_1{}^2$ | Digital movement $N/N_1{}^2$ |
|---|---|---|---|---|---|---|---|---|---|---|---|
| Levo-ketazocine | 1.0 | I.V. | 21.3 ±8.1 | — | — | — | — | — | 7 | 5/7 | 1/7 |
| Diazepam | 0.5 | I.H. | | | | | | | | | |

[1] Diazepam administered I.M. 30 minutes before levo-ketazocine
[2] $N/N_1$: N = No. of monkeys in which body jerks and/or digital movement was observed; $N_1$ = No. of monkeys tested.
[3] Mean ± 1 S.E.M.

Electroencephalographic Study in Monkeys

Electroencephalographic recordings of four Rhesus monkeys after intravenous doses of levo-ketazocine (0.25 mg/kg, 1 mg/kg, or 1 mg/kg thirty minutes after diazepam 0.5 mg/kg i.m.) showed high voltage rhythmic, bilaterally synchronous spike and wave discharge patterns, which were generally associated with minor clinical seizure phenomena, with durations of 10 seconds to 6 minutes, either without clinical components, or with eyelid flicker or other myoclonic activity or autonomic phenomena. Generalized slow atypical spike-wave activity, paroxysmal high voltage slow activity, and irregular slow, very high voltage rhythms with associated sedation/somnolence were seen elsewhere in the records. Hypertonus was generally associated with electrographic suppression or partial blocking and muscle potentials. Diazepam premedication did not prevent the EEG patterns but prolonged the portions of the records which were associated with sedation/somnolence.

The Compositions

Although any pharmaceutically acceptable salt of racemic ketazocine or levo-ketazocine is contemplated, the water-soluble salts are preferred, especially for intravenous administration. The methanesulfonate salt, which is described in Example 51 of U.S. Pat. No. 3,936,462, cited above at page 2, is particularly preferred. Although any pharmaceutically acceptable vehicle is contemplated, the preferred vehicle, especially for intravenous administration, is water. The formulation may also include physiological salts, antimicrobial preservatives, antioxidants and other pharmaceutical adjuncts and may be packaged in vials, ampules or disposable syringes.

Dose Ranges

In the tests in the dog and the monkey described above the range of doses of levo-ketazocine which produced anesthesia followed by recovery was 0.25-4 mg/kg, which shows that levo-ketazocine has a wide margin of safety in contrast to other intravenous anesthetics and from which it is contemplated that the corresponding dose range for humans would be on the order of 1-10 mg. for an adult as an intravenous bolus. Continuous infusion is also contemplated, but the effective dose rate has not been firmly established. In preliminary tests in the dog and the monkey infusion dose rates of 6, 12, 24, 72 and 84 mg/kg/hr of racemic ketazocine were tried. Dextroketazocine was subsequently found to have essentially no anesthetic effect in dogs. Thenceforth, only levo-ketazocine was evaluated. Thus, racemic ketazocine and levo-ketazocine appear to have a wide range of potential effectiveness and safety as intravenous anesthetics in doses on the order of 0.01-100 mg/kg.

For intramuscular administration in humans anesthetic doses of at least 1 mg of racemic ketazocine or levo-ketazocine are contemplated. The contemplated dose of diazepam as an intramuscular premedication in humans is the recommended dose of 10-20 mg for adults or 0.4 mg/kg for children over two years of age (AMA Drug Evaluations, Third Edition, Publishing Sciences Group, Inc., Littleton, Mass., 1977, p. 302).

Reversal of Anesthesia

A desired property of the ideal anesthetic is rapid recovery of consciousness. The use of narcotic antagonists, for example, naloxone, to reverse racemic ketazocine or levo-ketazocine anesthesia is contemplated. Naloxone was tried in preliminary tests in the dog and monkey and was found to reverse rapidly racemic-ketazocine anesthesia.

Four dogs were maintained unconscious by constant infusion of racemic ketazocine at 12 mg/kg/hr intravenously for one hour. At the end of this period, naloxone was administered at doses of 0.5 and 1.0 mg/kg intravenously to one and two dogs, respectively. The fourth dog received water intravenously to serve as control. The dogs given naloxone regained consciousness in 22 to 60 seconds postinjection (no dose response) and exhibited slight tremors and salivation for about the next 30 minutes. The control dog awakened after 25 minutes and exhibited faltering gait and partial miosis persisting for 90 minutes.

One monkey given naloxone, 1.0 mg/kg intravenously, after being maintained unconscious for 4 hours by infusion of racemic ketazocine at 12 mg/kg/hr intravenously, regained consciousness in 1-2 minutes. This monkey displayed marked muscle weakness and depression of locomotor activity for more than 3 hours, but recovered completely.

I claim:

1. The method of producing general anesthesia in a mammal in need of general anesthesia which comprises administering diazepam intramuscularly to the mammal and subsequently administering intravenously to the mammal an amount effective for producing general anesthesia of a pharmaceutically acceptable salt of racemic or levo 1,2,3,4,5,6-hexahydro-1-oxo-3-cyclopropylmethyl-8-hydroxy-6(eq),11(ax)-dimethyl-2,6-methano-3-benzazocine.

2. The method according to claim 1 wherein a pharmaceutically acceptable salt of levo 1,2,3,4,5,6-hexahydro-1-oxo-3-cyclopropylmethyl-8-hydroxy-6(eq),1-1(ax)-dimethyl-2,6-methano-3-benzazocine is used.

3. The method according to claim 2 wherein the levo 1,2,3,4,5,6-hexahydro-1-oxo-3-cyclopropylmethyl-8-hydroxy-6(eq),11(ax)-dimethyl-2,6-methano-3-benzazocine salt is levo 1,2,3,4,5,6-hexahydro-1-oxo-3-cyclopropylmethyl-8-hydroxy-6(eq),11(ax)-dimethyl-2,6-methano-3-benzazocine methanesulfonate.

* * * * *